United States Patent

Weitz et al.

[11] Patent Number: 4,618,704
[45] Date of Patent: Oct. 21, 1986

[54] ACYLOXY-2-BUTENES AND THEIR PREPARATION

[75] Inventors: Hans-Martin Weitz, Bad Durkheim; Rolf Fischer, Heidelberg, both of Fed. Rep. of Germany

[73] Assignee: BASF Aktiengesellschaft, Ludwigshafen, Fed. Rep. of Germany

[21] Appl. No.: 26,737

[22] Filed: Apr. 3, 1979

[30] Foreign Application Priority Data

May 5, 1978 [DE] Fed. Rep. of Germany ....... 2819592

[51] Int. Cl.[4] .................. C07C 67/055; C07C 69/10; C07C 69/18; C07C 69/30
[52] U.S. Cl. .................................. 560/262; 502/184; 502/185; 560/1; 560/112; 560/238
[58] Field of Search ........................... 560/262, 112, 1

[56] References Cited

U.S. PATENT DOCUMENTS 3,872,163 3/1975 Shimiza et al. .................... 560/244

FOREIGN PATENT DOCUMENTS 2217452 10/1972 Fed. Rep. of Germany ...... 560/261
2200124 7/1973 Fed. Rep. of Germany ...... 560/261
1447537 6/1966 France ............................. 560/261
1368505 9/1974 United Kingdom ............... 560/261

OTHER PUBLICATIONS

Chem. Abstracts, 66:104490P (1967).
Houben-Weyl, Methoden der Organ. Chemie, vol. V/1c, pp. 184–192.
J. Amer. Chem. Soc., 83, 1961, pp. 4916–4919.
Houben-Weyl, Methoden der Organ. Chemie, vol 7/1, p. 444.

Primary Examiner—Vivian Garner
Attorney, Agent, or Firm—Keil & Weinkauf

[57] ABSTRACT

Acyloxy-2-butenes of the formula

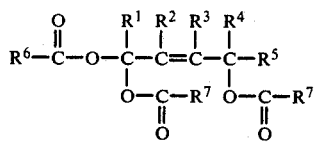

where $R^1$, $R^3$ and $R^4$ are each hydrogen or alkyl of 1 to 5 carbon atoms, $R^2$ is alkyl of 1 to 5 carbon atoms, $R^5$ is hydrogen, alkyl of 1 to 5 carbon atoms or $R^6$—CO—O, and $R^6$ and $R^7$ are each hydrogen, alkyl of 1 to 5 carbon atoms, phenyl or cyclohexyl, the preparation of these acyloxy-2-butenes by reaction of 1-acyloxy-1,3-butadienes of the formula

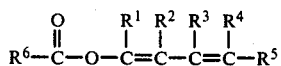

with carboxylic acids of the formula $R^7$—COOH and oxygen at 50°–180° C. in the presence of catalysts containing palladium or platinum, and the use of the compounds of the formula I, where $R^1$, $R^3$, $R^4$ and $R^5$ are hydrogen, $R^2$ and $R^6$ are methyl and $R^7$ is methyl or ethyl, for the preparation of 4-acyloxytiglic aldehydes.

3 Claims, No Drawings

ACYLOXY-2-BUTENES AND THEIR PREPARATION

The present invention relates to new acyloxy-2-butenes and their preparation by reaction of 1-acyloxy-1,3-butadienes with carboxylic acids and oxygen in the presence of catalysts.

1,4-Diacetoxy-2-butene, an important intermediate for the preparation of butanediol, is obtained, for example, by the process described in German Published Application DAS No. 2,217,452, which comprises reacting butadiene with acetic acid and oxygen in the presence of a palladium-containing catalyst. Isoprene, 2,3-dimethylbutadiene and piperylene can also be converted to the corresponding 1,4-diacetoxy-2-butenes by this process.

The present invention concerns acyloxy-2-butenes of the formula

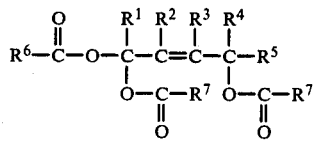
I where $R^1$, $R^3$ and $R^4$ are each hydrogen or alkyl of 1 to 5 carbon atoms, $R^2$ is alkyl of 1 to 5 carbon atoms, $R^5$ is hydrogen, alkyl of 1 to 5 carbon atoms or $R^6$—CO—O, and $R^6$ and $R^7$ are each hydrogen, alkyl of 1 to 5 carbon atoms, phenyl or cyclohexyl. These novel acyloxy-2-butenes are valuable intermediates, for example for the preparation of terpenes and drugs.

The 1,1,4-triacyloxy-2-alkyl-2-butenes and 1,1,4,4-tetraacyloxy-2-alkyl-2-butenes according to the invention are obtained by reacting a 1-acyloxy-1,3-butadiene of the formula

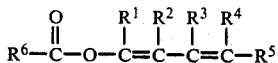
V where the radicals $R^1$ to $R^6$ have the abovementioned meanings, with oxygen and a carboxylic acid of the formula $$R^7\text{—COOH} \qquad \text{VI}$$

where $R^7$ has the abovementioned meanings, at from 50° to 180° C. and a pressure of from 1 to 100 bar in the presence of a catalyst containing palladium or platinum.

For the case of the preparation of 1,1,4-triacetoxy-2-methyl-2-butene the reaction can be represented by the following equation (—OAc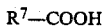—O—CO—CH$_3$):

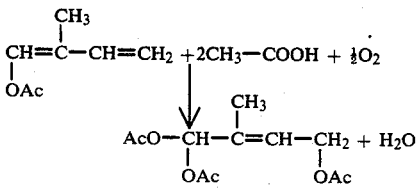

The outcome of the acyloxylation, according to the invention, of 1-acyloxy-2-alkyl-1,3-butadienes and 1,4-diacyloxy-2-alkyl-1,3-butadienes, resulting in the novel 1,1,4-triacyloxy-2-alkyl-2-butenes or 1,1,4,4-tetraacyloxy-2-alkyl-2-butenes, is surprising since, using the process described in German Laid-Open Application DOS No. 2,200,124, reaction of 1-acyloxy-1,3-butadienes with a carboxylic acid and oxygen in the presence of a palladium catalyst gives 1,4-diacyloxy-2-butenes.

The 1-acyloxy-1,3-butadienes required for the preparation of the novel 1,1,4-triacyloxy-2-butenes are obtainable by acylation of α,β-unsaturated aldehydes with acid anhydrides, acid halides, ketenes or enol-esters, such as 2-acetoxypropene (Houben-Weyl, Methoden der organischen Chemie, volume V/1 c, pages 184–192). For example, 1-acetoxy-2-methyl-1,3-butadiene can be prepared from tiglic aldehyde (α-methylcrotonaldehyde) or α-ethyl-acrolein.

The preferred carboxylic acids of the formula VI are formic acid and acids with alkyl radicals of 1 to 3 carbon atoms. For economic reasons, acetic acid is particularly preferred. The carboxylic acid is in general used in excess over the diene employed and hence at the same time serves as a reaction medium. However, it is also possible to carry out the reaction in a solvent which is inert under the reaction conditions, such as toluene, xylene, sulfolan or an ester, such as ethyl acetate or butenediol diacetate.

The reaction of the 1-acyloxy-1,3-butadienes with the carboxylic acids in order to prepare the 1,1,4-triacyloxy- or 1,1,4,4-tetraacyloxy-2-alkyl-2-butenes is carried out in the presence of oxygen and the catalyst, at from 50° to 180° C. In the gas phase, the temperature is preferably from 120° to 150° C., whilst in the liquid phase it is, for example, from 50° to 110° C. The reaction pressure depends on the procedure used and may be from atmospheric pressure to 100 bar. The reaction can be carried out batchwise or continuously, for example using a fixed bed, fluidized bed or three-phase fluidized bed.

Examples of suitable catalysts containing palladium or platinum are supported catalysts which in addition to palladium or platinum contain one or more of the elements antimony, bismuth, tellurium, selenium, sulfur, phosphorus, arsenic, iron, nickel, cobalt and copper. These include, for example, the supported catalysts mentioned in German Published Application DAS No. 2,217,452, which in addition to palladium contain one or more of the elements antimony, bismuth, tellurium and selenium, and the supported platinum catalysts described in German Laid-Open Application DOS No. 2,417,658, which additionally contain one of the elements phosphorus, arsenic, antimony, selenium or tellurium.

The use of supported catalysts is particularly advantageous. Such catalysts may be obtained in the conventional manner, for example by dispersing a carrier in a solution containing a palladium compound or platinum compound and one or more compounds of the transition metals, evaporating the solvent and reducing the residue in a stream of gas consisting, for example, of hydrogen or of nitrogen laden with a reducing compound, such as hydrazine, methanol or formaldehyde. The dried catalyst can also be reduced with liquid reducing agents. However, the catalyst can also be prepared by treating the carrier and solution conjointly with a precipitant, for example an alkaline precipitant, and isolating and reducing the precipitate.

A very advantageous method of preparation of the catalysts is to precipitate the metals from the aqueous solutions of their salts by means of reducing agents, such as formaldehyde, hydrazine and others, at a suitable pH (cf., for example, J. Amer. Chem. Soc., 83 (1961), 4,916) in the presence of the support. It is advisable additionally to heat the resulting crude catalysts to an elevated temperature in a stream of a reducing gas.

The palladium or platinum and the other elements can be deposited on the carrier simultaneously or in optional sequence. In some cases, the carrier can be added in the form of a soluble compound and be coprecipitated with the active metal.

Any reducing process by means of which the compounds used can be converted to the metal may be employed. Examples of suitable carriers are active charcoal, bauxite, pumice, silica gel, kieselguhr, silica, magnesia, clay and alumina. Where appropriate, the carriers can be made more suitable for their particular purpose by means of a conventional pretreatment, for example with an acid.

The choice of the palladium or platinum compound used to prepare the catalyst is not critical. For example, halogen-containing palladium or platinum compounds, e.g. palladium chloride and the platinum chlorides, salts of an organic acid, e.g. palladium acetate or platinum acetate, the nitrates, the oxides and the like may be used. However, other palladium or platinum compounds, especially complex compounds, for example hexachloroplatinic acid, sodium platinosulfate and ammonium hexachloroplatinate, may also be used as starting materials. The transition metals to be used as further constituents of the catalyst can also substantially be added in the form of compounds which can be selected freely. In general, soluble compounds will be used for convenience.

Usually, the amount of catalytically active metals on the carrier is from 0.1 to 20% by weight, based on the catalyst weight, but higher and lower concentrations can also be employed. The decision as to the most advantageous amount may also be determined by economic considerations. In case of doubt, the most advantageous amount can readily be established by exploratory experiments.

Amongst the supported catalysts consisting of palladium or platinum, on the one hand, and iron and/or copper, on the other, such as the palladium catalysts of the type described, those which contain active charcoal as the carrier and from about 1 to 20% of copper and/or from about 1 to 10% of iron, in addition to from 1 to 10% of palladium, based on the total catalyst weight, deserve special mention. Higher concentrations of palladium than those stated can be used but in general offer no particular advantage.

If the activity of the catalyst declines after a certain period of use, it can often be restored by suitable methods. For example, a deposit of polymeric compounds on the catalyst can be removed by means of suitable solvents or by careful treatment with oxygen-containing gases. If the activity of the catalyst has been reduced by oxidation phenomena, regeneration is frequently feasible by treatment with reducing compounds, e.g. hydrazine, formaldehyde, hydrogen, carbon monoxide or methanol (vapor).

Oxygen is employed in the stoichiometric amount or in excess. It is also possible to employ oxygen mixed with an inert gas, such as nitrogen or carbon dioxide.

In batchwise operation, the reaction is carried out, for example, as follows. Oxygen and the 1-acyloxy-1,3-butadiene are fed to a suspension of the catalyst in the particular carboxylic acid at the reaction temperature and the reaction pressure. After completion of the addition, stirring is continued if appropriate. The reaction mixture is cooled to room temperature and nitrogen is passed through it. The catalyst is then separated off and the mixture is subjected to fractional distillation. In the course thereof, unconverted starting compounds, and any 4-acyloxy-2-butenals formed, are separated from the process products. Unconsumed 1-acyloxy-1,3-butadiene can be returned to the acyloxylation stage.

In continuous operation, the mixture of 1-acyloxy-1,3-diene, carboxylic acid and oxygen can be passed over the fixed catalyst, for example using the ascending flow method or trickle method.

The novel 1,1,4-triacyloxy compounds and 1,1,4,4-tetraacyloxy compounds are obtained with high selectivity by the process according to the invention.

Amongst the novel acyloxy-2-butenes, the compounds of the formula

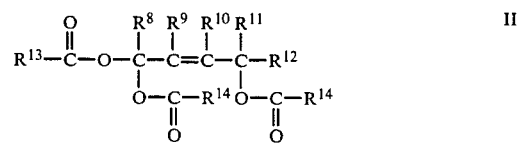

where $R^8$ and $R^{10}$ to $R^{14}$ are each hydrogen or alkyl of 1 to 3 carbon atoms and $R^9$ is alkyl of 1 to 3 carbon atoms, are preferred. Compounds of very particular industrial interest are those of the formula

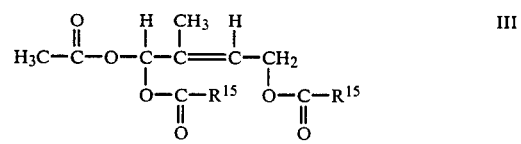

where $R^{15}$ is hydrogen, methyl or ethyl.

Since the novel 1,1,4-triacyloxy-2-butenes can easily be hydrolyzed to the corresponding 4-acyloxy-2-butenals, the present invention provides a novel, advantageous method of synthesis which, for example, leads from tiglic aldehyde (VII) via 1-acetoxy-2-methyl-1,3-butadiene (VIII), obtainable by conventional acetylation, to the highly sought-after compound 4-acetoxytiglic aldehyde (IX).

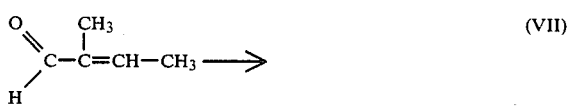

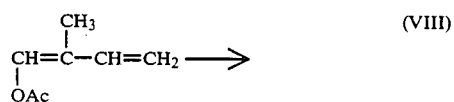

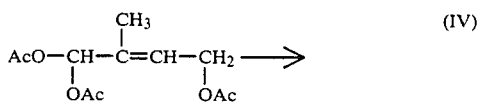

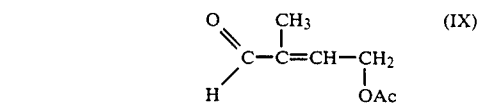

This new method of synthesis amounts to an oxidation of a methyl, methylene or methyne group in 2-butenals, since formally a

group is oxidized to a

group.

Accordingly, a further advantageous embodiment of the invention relates to the use of the novel 1,1,4-triacyloxy-2-butenes for the preparation of 4-acyloxy-2-butenals. In this context, the use of the compounds of the formula III for the preparation of 4-acyloxytiglic aldehydes of the formula IX, which serve as $C_5$ units for the synthesis of vitamin A acetate, is of particular interest. The hydrolysis of 1,1,4-triacyloxy-2-methyl-2-butenes to 4-acyloxytiglic aldehydes is carried out by conventional method, for example by treatment with acids or bases (Houben-Weyl, Methoden der organischen Chemie, volume 7/1, page 444). It is also possible directly to hydrolyze the reaction mixture obtained on preparation of the acyloxy-2-butenes according to the invention, of the formula III, with or without prior removal of the catalyst and of the unconsumed starting compounds, to give the corresponding 4-acyloxy-2-butenals. Since the acyloxylation results in one mole of water per mole of 1,1,4-triacyloxy-2-butene formed, sufficient water for the hydrolysis of the acylal is present. Hence, a certain amount of 4-acyloxy-2-butenal is already detectable by gas chromatography after the acyloxylation, alongside 1,1,4-triacyloxy-2-butene. The hydrolysis can be accelerated by adding water and/or hydrolysis catalysts and carrying out the reaction under atmospheric pressure at from 20° C. to the boiling point of the particular carboxylic acid, or under pressure at above the said boiling point.

In the Examples, parts are by weight.

EXAMPLE 1

1,1,4-Triacetoxy-2-methyl-2-butene (Pd-Cu catalyst)

(a) Preparation of the catalyst 4.48 parts of copper powder, dissolved in 42 parts by volume of 33% strength nitric acid, are added, at room temperature, to 5.31 parts of palladium acetate dissolved in 75 parts by volume of 50% strength ethanol. This salt solution is added, at room temperature, to 50 parts of active charcoal (0.3–0.5 mm, 35–50 mesh), which has beforehand been mixed at room temperature with 160 parts by volume of 15% strength nitric acid, heated to 70° C., stirred for 5 hours at this temperature, cooled, collected on a glass suction filter, washed with water until the pH is 7–8 and dried for 16 hours in an oven under reduced pressure. The mixture of salt solution and active charcoal is evaporated to dryness at 85° C. on a rotary evaporator (under a water pump vacuum).

The catalyst is dried for 2 hours at 150° C. in an oven under reduced pressure and then for 2 hours at 150° C. in a tubular oven under a stream of nitrogen. The catalyst is then activated for 6 hours at 200° C., followed by 6 hours at 400° C., with nitrogen which has been saturated with methanol at room temperature, and finally for 0.5 hour with hydrogen (20,000 parts by volume/hour) at 800° C. It is allowed to cool to room temperature under a stream of nitrogen and stored under argon in a well-sealed bottle.

X-Ray analysis of the catalyst shows that it contains a $PdCu_3$ phase with a small amount of PdCu.

(b) Preparation of 1,1,4-triacetoxy-2-methyl-2-butene 15 parts of the catalyst, suspended in 600 parts of glacial acetic acid, are introduced into a three-necked flask equipped with a gassing stirrer, internal thermometer, reflux condenser, gas inlet tube and dropping funnel, and are warmed to 95° C. (oil bath) under a stream of nitrogen. 67.5 parts of 1-acetoxy-2-methyl-1,3-butadiene, from the dropping funnel, and 12,000 parts by volume of oxygen, through the gas inlet tube, are then introduced simultaneously, uniformly distributed over 4 hours, at the above temperature. Ater completion of addition of the starting materials, the mixture is stirred for a further 15 minutes whilst passing nitrogen through it, after which it is allowed to cool to room temperature and the catalyst is filtered off on a glass suction filter. This gives 668 parts of a reaction product which according to analysis by gas chromatography has the following composition:

trans- +cis-1,1,4-triacetoxy-2-methyl-2-butene: 6.50% by weight trans- +cis-4-acetoxytiglic aldehyde: 1.90% by weight unconverted 1-acetoxy-2-methyl-1,3-butadiene: 3.96% by weight tiglic aldehyde: 0.26% by weight diacetoxy-2-methyl-1,3-butadiene: 0.30% by weight unknown compounds: 0.50% by weight glacial acetic acid: remainder Fractional distillation of the reaction mixture gives 39.5 parts of 1,1,4-triacetoxy-2-methyl-2-butene of boiling point 104°–111° C./0.3 mbar ($n_D^{20}=1.4493$) (representing 30.2% conversion). The yield of 1,1,4-triacetoxy-2-methyl-2-butene and 4-acetoxytiglic aldehyde together is 87.7%, based on the amount of tiglic aldehyde and 1-acetoxy-2-methyl-1,3-butadiene present, according to gas chromatography, in the starting material.

EXAMPLE 2

1,1,4-Triacetoxy-2-methyl-2-butene (Pd-Te catalyst)

Following the method described in Example 1, 15 parts of a palladium-tellurium catalyst with active charcoal (0.2–0.4 mm) as the carrier, the catalyst being prepared as described in German Published Application DAS No. 2,217,452 and containing 5% of Pd and 1% of Te, are suspended in 600 parts of glacial acetic acid and used for reaction with 34 parts of 1-acetoxy-2-methyl-1,3-butadiene and 6,000 parts by volume of oxygen in the course of 2 hours at 95° C. After working up as described in Example 1b, and distilling the product, 18.6 parts of 1,1,4-triacetoxy-2-methyl-2-butene of boiling point 105°–112° C./0.4 mbar ($n_D^{20}=1.4492$) (representing 28.2% conversion) are obtained in addition to unconverted starting material.

EXAMPLE 3

1,1,4-Triacetoxy-2-methyl-2-butene (Pt-Te catalyst)

The procedure described in Example 2 is followed, except that 15 parts of a platinum-tellurium catalyst with active charcoal (0.2-0.4 mm) as the carrier, the catalyst being prepared as described in German Laid-Open Application DOS No. 2,417,658 and containing 4.9% of Pt and 1.0% of Te, are used. 8.7 parts of 1,1,4-triacetoxy-2-methyl-2-butene of boiling point 114°-120° C./0.7 mbar ($n_D^{20} = 1.4489$) (representing 13.2% conversion) are obtained.

EXAMPLE 4

1,1,4-Triacetoxy-2-methyl-2-butene (Pd-Cu catalyst)

12,000 parts by volume of oxygen are introduced in the course of 4 hours into a solution, at 95° C., of 63 parts of 1-acetoxy-2-methyl-1,3-butadiene in 600 parts of glacial acetic acid, in which 25 parts of the catalyst prepared as described in Example 1a are suspended. The reaction mixture is worked up as described in Example 1b and fractional distillation gives 71.8 parts of 1,1,4-triacetoxy-2-methyl-2-butene (representing 58.8% conversion) of boiling point 118°-124° C./0.7 mbar and 19.5 parts of 4-acetoxytiglic aldehyde (representing 27.4% conversion) of boiling point 102°-107° C./25-27 mbar.

EXAMPLE 5

Use of 1,1,4-triacetoxy-2-methyl-2-butene for the preparation of 4-acetoxytiglic aldehyde Following the procedure described in Example 1b, 67.5 parts of 1-acetoxy-2-methyl-1,3-butadiene in 600 parts of glacial acetic acid are reacted with 12,000 parts by volume of oxygen in the presence of 15 parts of the catalyst prepared as described in Example 1a. After completion of addition of the diene, a further 6,000 parts by volume of oxygen are introduced in the course of 2 hours at 95° C. The mixture is then stirred for a further 15 minutes whilst passing nitrogen through, after which it is allowed to cool to room temperature, the catalyst is filtered off, 28.9 l parts of water are added to the filtrate and this mixture is refluxed for 10 hours. Fractional distillation gives 49.4 parts of trans-4-acetoxytiglic aldehyde (representing 65% conversion) of boiling point 105°-107° C./27 mbar, $n_D^{20} = 1.4640$.

We claim:

1. 1,1,4-Triacyloxy-2-methyl-2-butenes of the formula

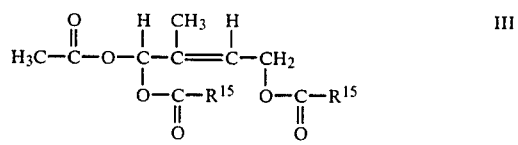

III where $R^{15}$ is hydrogen, methyl or ethyl.

2. 1,1,4-Triacetoxy-2-methyl-2-butene of the formula

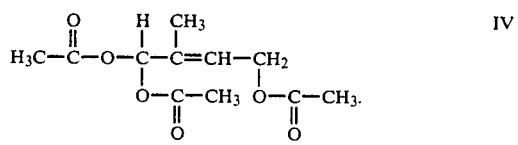

IV

3. A process for the preparation of 1,1,4-triacetoxy-2-methyl-2-butene of the formula

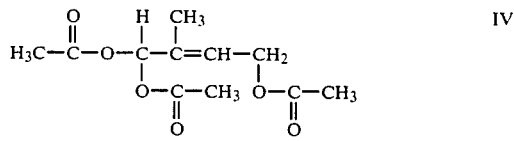

IV which comprises reacting

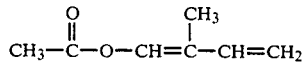

with $CH_3$—$COOH$ and oxygen at a temperature of from 50° to 180° C. and a pressure of from 1 to 100 bar in the presence of a catalyst containing palladium or platinum.

* * * * *